US009775996B2

(12) United States Patent
Gross (10) Patent No.: US 9,775,996 B2
(45) Date of Patent: *Oct. 3, 2017

(54) ELECTRICAL TREATMENT OF ALZHEIMER'S DISEASE

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,290

(22) Filed: Mar. 8, 2017

(65) Prior Publication Data
US 2017/0173331 A1    Jun. 22, 2017

Related U.S. Application Data

(63) Continuation of application No. 14/794,739, filed on Jul. 8, 2015, now Pat. No. 9,616,221.

(51) Int. Cl.
*A61N 1/36* (2006.01)
*A61N 1/05* (2006.01)
*A61N 1/20* (2006.01)

(52) U.S. Cl.
CPC ....... *A61N 1/36025* (2013.01); *A61N 1/0529* (2013.01); *A61N 1/20* (2013.01)

(58) Field of Classification Search
None
See application file for complete search history.

(56) References Cited

U.S. PATENT DOCUMENTS

| 4,503,863 | A | 3/1985 | Katims |
| 5,088,977 | A | 2/1992 | Sibalis |
| 5,121,754 | A | 6/1992 | Mullett |
| 5,529,574 | A | 6/1996 | Frackelton |
| 5,792,100 | A | 8/1998 | Shantha |

(Continued)

FOREIGN PATENT DOCUMENTS

| WO | 01/52931 | 7/2001 |
| WO | 01/85027 | 11/2001 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Ankit D Tejani
(74) *Attorney, Agent, or Firm* — Sughrue Mion, PLLC (57) ABSTRACT

Apparatus is provided that includes midplane treatment electrodes, configured to be disposed over a superior sagittal sinus, outside and in electrical contact with a skull of a head of a subject identified as at risk of or suffering from Alzheimer's disease; and lateral treatment electrodes, configured to be disposed between 1 and 12 cm of a sagittal midplane of the skull. Control circuitry is configured to treat the subject by electroosmotically driving fluid from a subarachnoid space to the superior sagittal sinus, by applying one or more treatment currents between (a) one or more of the midplane treatment electrodes and (b) one or more of the lateral treatment electrodes.

24 Claims, 5 Drawing Sheets

(56) References Cited

U.S. PATENT DOCUMENTS

| | | | |
|---|---|---|---|
| 5,911,223 | A | 6/1999 | Weaver et al. |
| 6,041,252 | A | 3/2000 | Walker et al. |
| 6,161,047 | A | 12/2000 | King et al. |
| 6,567,702 | B1 | 5/2003 | Nekhendzy et al. |
| 6,591,138 | B1 | 7/2003 | Fischell et al. |
| 6,602,248 | B1 | 8/2003 | Sharps et al. |
| 6,941,172 | B2 | 9/2005 | Nachum |
| 6,997,941 | B2 | 2/2006 | Sharkey et al. |
| 7,120,489 | B2 | 10/2006 | Shalev et al. |
| 7,398,121 | B2 | 7/2008 | Matsumura et al. |
| 7,509,171 | B2 | 3/2009 | DiMauro |
| 7,640,062 | B2 | 12/2009 | Shalev |
| 7,860,569 | B2 | 12/2010 | Solberg et al. |
| 8,190,248 | B2 | 5/2012 | Besio et al. |
| 8,457,761 | B2 | 6/2013 | Wariar |
| 8,577,469 | B2 | 11/2013 | Gross |
| 8,676,348 | B2 | 3/2014 | Gross |
| 9,616,221 | B2 * | 4/2017 | Gross ................... A61N 1/30 |
| 2002/0151948 | A1 | 10/2002 | King et al. |
| 2002/0183683 | A1 | 12/2002 | Lerner |
| 2003/0130707 | A1 | 7/2003 | Gan et al. |
| 2003/0158589 | A1 | 8/2003 | Katsnelson |
| 2003/0216792 | A1 | 11/2003 | Levin et al. |
| 2003/0225331 | A1 | 12/2003 | Diederich et al. |
| 2004/0002746 | A1 | 1/2004 | Ryan et al. |
| 2004/0019381 | A1 | 1/2004 | Pflueger |
| 2004/0049180 | A1 | 3/2004 | Sharps et al. |
| 2004/0116977 | A1 | 6/2004 | Finch et al. |
| 2004/0210209 | A1 | 10/2004 | Yeung et al. |
| 2005/0010205 | A1 | 1/2005 | Hovda et al. |
| 2005/0021104 | A1 | 1/2005 | DiLorenzo |
| 2005/0159790 | A1 | 7/2005 | Shalev |
| 2005/0277996 | A1 | 12/2005 | Podhajsky et al. |
| 2006/0030895 | A1 | 2/2006 | Simon et al. |
| 2006/0106430 | A1 | 5/2006 | Fowler et al. |
| 2006/0224223 | A1 | 10/2006 | Podhajsky et al. |
| 2006/0293723 | A1 | 12/2006 | Whitehurst et al. |
| 2007/0000784 | A1 | 1/2007 | Paul et al. |
| 2007/0073402 | A1 | 3/2007 | Vresilovic et al. |
| 2007/0213700 | A1 | 9/2007 | Davison et al. |
| 2008/0119907 | A1 | 5/2008 | Stahmann |
| 2008/0260542 | A1 | 10/2008 | Nishikawa et al. |
| 2009/0112278 | A1 | 4/2009 | Wingeier et al. |
| 2009/0125080 | A1 | 5/2009 | Montgomery |
| 2009/0126813 | A1 | 5/2009 | Yanagisawa et al. |
| 2009/0131850 | A1 | 5/2009 | Geiger |
| 2009/0312816 | A1 | 12/2009 | Gross |
| 2010/0217369 | A1 | 8/2010 | Gross |
| 2010/0324441 | A1 | 12/2010 | Hargrove et al. |
| 2011/0046540 | A1 | 2/2011 | Alterman et al. |
| 2011/0160638 | A1 | 6/2011 | Mauge et al. |
| 2011/0160797 | A1 | 6/2011 | Makous et al. |
| 2013/0066392 | A1 * | 3/2013 | Simon ................... A61N 1/40 607/45 |
| 2013/0166006 | A1 | 6/2013 | Williams |
| 2014/0058189 | A1 * | 2/2014 | Stubbeman ............ A61N 2/002 600/13 |
| 2014/0088672 | A1 * | 3/2014 | Bedenbaugh ........ A61B 5/0478 607/116 |
| 2014/0207224 | A1 | 7/2014 | Simon |
| 2014/0257168 | A1 | 9/2014 | Gill |
| 2014/0324128 | A1 * | 10/2014 | Gross ................... A61N 1/327 607/62 |
| 2015/0011927 | A1 | 1/2015 | Hua |
| 2015/0119898 | A1 | 4/2015 | Desalles et al. |
| 2017/0007823 | A1 | 1/2017 | Gross |
| 2017/0120053 | A1 | 5/2017 | Fostick et al. |

FOREIGN PATENT DOCUMENTS

| | | |
|---|---|---|
| WO | 01/85094 | 11/2001 |
| WO | 2006/090397 | 8/2006 |
| WO | 2008/007369 | 1/2008 |
| WO | 2017/072769 | 5/2017 |

OTHER PUBLICATIONS

De La Torre JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

An Office Action dated Apr. 11, 2013, which issued during the prosecution of U.S. Appl. No. 13/663,757.

Notice of Allowance dated of Oct. 28, 2013, which issued during the prosecution U.S. Appl. No. 13/663,757.

Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.

An Applicant Initiated Interview Summary dated Dec. 14, 2015, which issued during the prosecution of U.S. Appl. No. 13/872,794.

An Office Action dated Feb. 3, 2016, which issued during the prosecution of U.S. Appl. No. 13/872,794.

Notice of Allowance dated Dec. 9, 2016, which issued during the prosecution of U.S. Appl. No. 14/794,739.

An Applicant Initiated Interview Summary dated Feb. 25, 2016, which issued during the prosecution of U.S. Appl. No. 13/872,794.

An Office Action dated Jun. 15, 2016, which issued during the prosecution of U.S. Appl. No. 13/872,794.

An International Search Report and a Written Opinion both dated Oct. 20, 2016, which issued during the prosecution of Applicant's PCT/IL2016/050728.

An Office Action dated Sep. 21, 2016, which issued during the prosecution of U.S. Appl. No. 14/794,739.

An International Search Report and a Written Opinion both dated Jan. 26, 2017, which issued during the prosecution of Applicant's PCT/IL2016/051161.

* cited by examiner

ELECTRICAL TREATMENT OF ALZHEIMER'S DISEASE

CROSS-REFERENCE TO RELATED APPLICATIONS

The present application is a continuation of U.S. application Ser. No. 14/794,739, filed Jul. 8, 2015, now U.S. Pat. No. 9,616,221.

FIELD OF THE APPLICATION

The present invention relates generally to treatment and prevention of Alzheimer's diseases, and specifically to electrical techniques for treating and preventing Alzheimer's disease.

BACKGROUND OF THE APPLICATION

Alzheimer's disease is a chronic neurodegenerative disease that causes dementia. Accumulation of amyloid beta in the brain is widely believed to contribute to the development of Alzheimer's disease.

SUMMARY OF THE APPLICATION

Embodiments of the present invention provide a system and methods for treating Alzheimer's disease. The system comprises a plurality of midplane treatment electrodes, a plurality of lateral treatment electrodes, and control circuitry, which is electrically coupled to the treatment electrodes. For some applications, a method for treating Alzheimer's disease comprises:
  disposing the midplane treatment electrodes over a superior sagittal sinus, outside and in electrical contact with a skull of a head of a subject identified as at risk of or suffering from Alzheimer's disease;
  disposing the lateral treatment electrodes between 1 and 12 cm of a sagittal midplane of the skull; and
  treating the subject by electroosmotically driving fluid from a subarachnoid space to the superior sagittal sinus, by activating the control circuitry to apply one or more treatment currents between (a) one or more of the midplane treatment electrodes and (b) one or more of the lateral treatment electrodes.

For some applications, treating the subject comprises facilitating clearance of amyloid beta from the subarachnoid space to the superior sagittal sinus by electroosmotically driving the fluid from the subarachnoid space to the superior sagittal sinus. Alternatively or additionally, for some applications, treating the subject comprises facilitating clearance of metal ions from the subarachnoid space to the superior sagittal sinus by electroosmotically driving the fluid from the subarachnoid space to the superior sagittal sinus.

Avoiding insertion of midplane treatment electrodes into the superior sagittal sinus may reduce any risks associated with implantation and operation of the system.

Typically, the control circuitry is activated to configure the midplane treatment electrodes as cathodes, and the lateral treatment electrodes as anodes. For some applications, the control circuitry is activated to independently apply the treatment currents between respective pairs of the midplane and the lateral treatment electrodes.

For some applications, the one or more treatment currents applied using the midplane and the lateral treatment electrodes pass between the subarachnoid space and the superior sagittal sinus, via inferolateral surfaces of the superior sagittal sinus. For these applications, the locations of the midplane treatment electrodes and/or the lateral treatment electrodes are typically selected such that the one or more treatment currents pass through the inferolateral surfaces. For example, for configurations in which the lateral treatment electrodes are disposed outside and in electrical contact with the skull, the lateral treatment electrodes may be disposed between 5 and 12 cm of the sagittal midplane of the skull; for configurations in which the lateral treatment electrodes are implanted under an arachnoid mater of the subject, the lateral treatment electrodes may be disposed between 1 and 3 cm of the sagittal midplane of the skull.

For some applications, the midplane treatment electrodes are disposed outside the head, such as on an external surface of the head. For other applications, the midplane treatment electrodes are implanted under skin of the head. For some applications, the system further comprises a midplane lead, along which the midplane treatment electrodes are disposed (e.g., fixed).

For some applications, the lateral treatment electrodes are disposed outside and in electrical contact with the skull. For some of these applications, the lateral treatment electrodes are disposed outside the head, such as on the external surface of the head, or are implanted under the skin of the head.

For some applications, the lateral treatment electrodes comprise left lateral treatment electrodes and right lateral treatment electrodes. The left lateral treatment electrodes are disposed left of the sagittal midplane of the skull, and the right lateral treatment electrodes are disposed right of the sagittal midplane of the skull. For some applications, the control circuitry is activated to configure the midplane treatment electrodes as cathodes, and the left and the right lateral treatment electrodes as left and right anodes, respectively.

For some applications, the lateral treatment electrodes are implanted under arachnoid mater of the subject, such as in the subarachnoid space or in gray or white matter of a brain of the subject.

There is therefore provided, in accordance with an application of the present invention, a method including:
  disposing midplane treatment electrodes over a superior sagittal sinus, outside and in electrical contact with a skull of a head of a subject identified as at risk of or suffering from Alzheimer's disease;
  disposing lateral treatment electrodes between 1 and 12 cm of a sagittal midplane of the skull; and
  treating the subject by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes.

For some applications, treating the subject includes facilitating clearance of amyloid beta from the subarachnoid space to the superior sagittal sinus by electroosmotically driving the fluid from the subarachnoid space to the superior sagittal sinus. Alternatively or additionally, for some applications, treating the subject includes facilitating clearance of metal ions from the subarachnoid space to the superior sagittal sinus by electroosmotically driving the fluid from the subarachnoid space to the superior sagittal sinus.

For some applications, activating the control circuitry includes activating the control circuitry to apply the one or more treatment currents with an average amplitude of between 1 and 3 milliamps.

For some applications, disposing the lateral treatment electrodes includes disposing the lateral treatment electrodes outside and in electrical contact with the skull. For some applications, disposing the lateral treatment electrodes includes disposing the lateral treatment electrodes between 4 and 12 cm of the sagittal midplane of the skull. For some applications, disposing the midplane and the lateral treatment electrodes includes disposing each of the lateral treatment electrodes between 1 and 12 cm of at least one of the midplane treatment electrodes. For some applications, disposing the midplane and the lateral treatment electrodes includes disposing each of the lateral treatment electrodes between 1 and 12 cm of one of the midplane treatment electrodes that is closest to the lateral treatment electrode.

For some applications, disposing the lateral treatment electrodes includes disposing the lateral treatment electrodes outside the head. For some applications, disposing the lateral treatment electrodes includes disposing the lateral treatment electrodes on an external surface of the head. For some applications, disposing the lateral treatment electrodes includes implanting the lateral treatment electrodes under skin of the head.

For some applications, disposing the midplane treatment electrodes includes disposing the midplane treatment electrodes outside the head. For some applications, disposing the midplane treatment electrodes includes disposing the midplane treatment electrodes on an external surface of the head. For some applications, disposing the midplane treatment electrodes includes implanting the midplane treatment electrodes under skin of the head.

For some applications, disposing the lateral treatment electrodes includes implanting the lateral treatment electrodes under an arachnoid mater of the subject. For some applications, disposing the lateral treatment electrodes includes disposing the lateral treatment electrodes between 1 and 3 cm of the sagittal midplane of the skull. For some applications, disposing the midplane and the lateral treatment electrodes includes disposing each of the lateral treatment electrodes between 1 and 3 cm of at least one of the midplane treatment electrodes. For some applications, disposing the midplane and the lateral treatment electrodes includes disposing each of the lateral treatment electrodes between 1 and 3 cm of one of the midplane treatment electrodes that is closest to the lateral treatment electrode. For some applications, disposing the lateral treatment electrodes includes disposing the lateral treatment electrodes in the subarachnoid space. For some applications, disposing the lateral treatment electrodes includes disposing the lateral treatment electrodes in gray or white matter of a brain of the subject.

For some applications, disposing the midplane treatment electrodes includes disposing the midplane treatment electrodes within 10 mm of the sagittal midplane of the skull.

For some applications, the method further includes implanting the control circuitry under skin of the subject.

For some applications, disposing the midplane treatment electrodes includes disposing the midplane treatment electrodes such that at least one of the midplane treatment electrodes is at least 5 mm from another one of the midplane treatment electrodes. For some applications, disposing the lateral treatment electrodes includes disposing the lateral treatment electrodes such that at least one of the lateral treatment electrodes is at least 5 mm from another one of the lateral treatment electrodes.

For some applications, disposing the midplane treatment electrodes includes disposing at least five midplane treatment electrodes over the superior sagittal sinus. For some applications, disposing the lateral treatment electrodes includes disposing at least five lateral treatment electrodes between 1 and 12 cm of the sagittal midplane of the skull.

For some applications:
  disposing the midplane treatment electrodes includes disposing a midplane lead outside the skull, and the midplane treatment electrodes are disposed along the midplane lead, and
  disposing the lateral treatment electrodes includes disposing a lateral lead within 1 and 12 cm of the sagittal midplane of the skull, and the lateral treatment electrodes are disposed along the lateral lead.

For some applications, activating the control circuitry includes activating the control circuitry to configure the midplane treatment electrodes as cathodes, and the lateral treatment electrodes as anodes.

For some applications:
  the lateral treatment electrodes include left lateral treatment electrodes and right lateral treatment electrodes, and
  disposing the lateral treatment electrodes includes disposing the left lateral treatment electrodes left of the sagittal midplane of the skull, and disposing the right lateral treatment electrodes right of the sagittal midplane of the skull.

For some applications, activating the control circuitry includes activating the control circuitry to configure the midplane treatment electrodes as cathodes, and the left and the right lateral treatment electrodes as left and right anodes, respectively.

For some applications:
  disposing the left lateral treatment electrodes includes disposing the left lateral treatment electrodes such that at least one of the left lateral treatment electrodes is at least 1 cm from another one of the left lateral treatment electrodes, and
  disposing the right lateral treatment electrodes includes disposing the right lateral treatment electrodes such that at least one of the right lateral treatment electrodes is at least 1 cm from another one of the right lateral treatment electrodes.

For some applications:
  disposing the left lateral treatment electrodes includes disposing at least five left lateral treatment electrodes left of the sagittal midplane of the skull, and
  disposing the right lateral treatment electrodes includes disposing at least five right lateral treatment electrodes right of the sagittal midplane of the skull.

For some applications:
  disposing the midplane treatment electrodes includes disposing a midplane lead outside the skull, and the midplane treatment electrodes are disposed along the lead,
  disposing the left lateral treatment electrodes includes disposing a left lateral lead outside the skull, and the left lateral treatment electrodes are disposed along the left lateral lead, and
  disposing the right lateral treatment electrodes includes disposing a right lateral lead outside the skull, and the right lateral treatment electrodes are disposed along the right lateral lead.

For some applications, activating the control circuitry to apply the one or more treatment currents between (a) one or more of the midplane treatment electrodes and (b) one or more of the lateral treatment electrodes includes activating the control circuitry to apply:
  a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

For some applications, activating the control circuitry includes activating the control circuitry to configure the midplane treatment electrodes as cathodes, and the left and the right lateral treatment electrodes as left and right anodes, respectively.

For some applications, electroosmotically driving the fluid includes:

detecting, by the control circuitry, a voltage difference between the subarachnoid space and the superior sagittal sinus; and setting, by the control circuitry, a level of the one or more treatment currents responsively to the detected voltage difference.

For some applications:

the method further includes implanting a single first detection electrode in the subarachnoid space, and a single second detection electrode in the superior sagittal sinus, and detecting the voltage includes detecting, by the control circuitry, the voltage difference between the first and the second detection electrodes.

For some applications, activating the control circuitry includes activating the control circuitry to apply the one or more treatment currents as direct current. For some applications, activating the control circuitry includes activating the control circuitry to apply the one or more direct currents as a plurality of pulses.

There is further provided, in accordance with an application of the present invention, a method including:

disposing one or more midplane treatment electrodes over a superior sagittal sinus, outside and in electrical contact with a skull of a head of a subject identified as at risk of or suffering from Alzheimer's disease;

disposing one or more lateral treatment electrodes between 1 and 12 cm of a sagittal midplane of the skull; and treating the subject by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes.

For some applications:

the one or more lateral treatment electrodes include one or more left lateral treatment electrodes and one or more right lateral treatment electrodes, and disposing the one or more lateral treatment electrodes includes disposing the one or more left lateral treatment electrodes left of the sagittal midplane of the skull, and disposing the one or more right lateral treatment electrodes right of the sagittal midplane of the skull.

For some applications, activating the control circuitry includes activating the control circuitry to configure the one or more midplane treatment electrodes as one or more cathodes, the one or more left lateral treatment electrodes as one or more left anodes, and the one or more right lateral treatment electrodes as one or more right anodes.

For some applications, the one or more midplane treatment electrodes include an elongate electrode having a length of at least 10 cm. For some applications, the one or more lateral treatment electrodes include an elongate electrode having a length of at least 10 cm.

There is further provided, in accordance with an application of the present invention, apparatus for treating a subject identified as at risk of or suffering from Alzheimer's disease, the apparatus including:

exactly three leads, consisting of a midplane lead, a left lateral lead, and a right lateral lead;

at least five midplane electrodes, which are disposed along the midplane lead at an average distance of at least 1 cm between longitudinally-adjacent pairs of the midplane electrodes, measured between longitudinal midpoints of the midplane electrodes;

at least five left lateral electrodes, which are disposed along the left lateral lead at an average distance of at least 1 cm between longitudinally-adjacent pairs of the left lateral electrodes, measured between longitudinal midpoints of the left lateral electrodes;

at least five right lateral electrodes, which are disposed along the right lateral lead at an average distance of at least 1 cm between longitudinally-adjacent pairs of the right lateral electrodes, measured between longitudinal midpoints of the right lateral electrodes; and a housing, which includes control circuitry, to which the midplane, the left lateral, and the right lateral electrodes are electrically coupled via the midplane lead, the left lateral lead, and the right lateral lead, respectively, the control circuitry configured to:

configure the midplane treatment electrodes as cathodes, and the left and the right lateral treatment electrodes as left and right anodes, respectively, apply respective treatment currents between (a) (i) one or more of the midplane treatment electrodes and (ii) one or more of the left lateral treatment electrodes, and (b) (i) one or more of the midplane treatment electrodes and (ii) one or more of the right lateral treatment electrodes, and configure the treatment currents to treat the subject by electroosmotically driving fluid from a subarachnoid space to a superior sagittal sinus of the subject.

For some applications, the control circuitry is configured to apply the treatment currents with an average amplitude of between 1 and 3 milliamps.

For some applications, the housing is configured to be implanted under skin of the subject.

For some applications, the control circuitry is configured to apply:

a first treatment current between a first one of the midplane treatment electrodes and a first one of the left lateral treatment electrodes, a second treatment current between the first one of the midplane treatment electrodes and a first one of the right lateral treatment electrodes, a third treatment current between a second one of the midplane treatment electrodes and a second one of the left lateral treatment electrodes, and a fourth treatment current between the second one of the midplane treatment electrodes and a second one of the right lateral treatment electrodes.

For some applications, the control circuitry is configured to:

detect a voltage difference between the subarachnoid space and the superior sagittal sinus; and set a level of the treatment currents responsively to the detected voltage difference.

For some applications, the control circuitry is configured to apply the treatment currents as direct current. For some applications, the control circuitry is configured to apply the direct currents as a plurality of pulses.

The present invention will be more fully understood from the following detailed description of embodiments thereof, taken together with the drawings, in which:

DETAILED DESCRIPTION OF APPLICATIONS

Figure 1A:
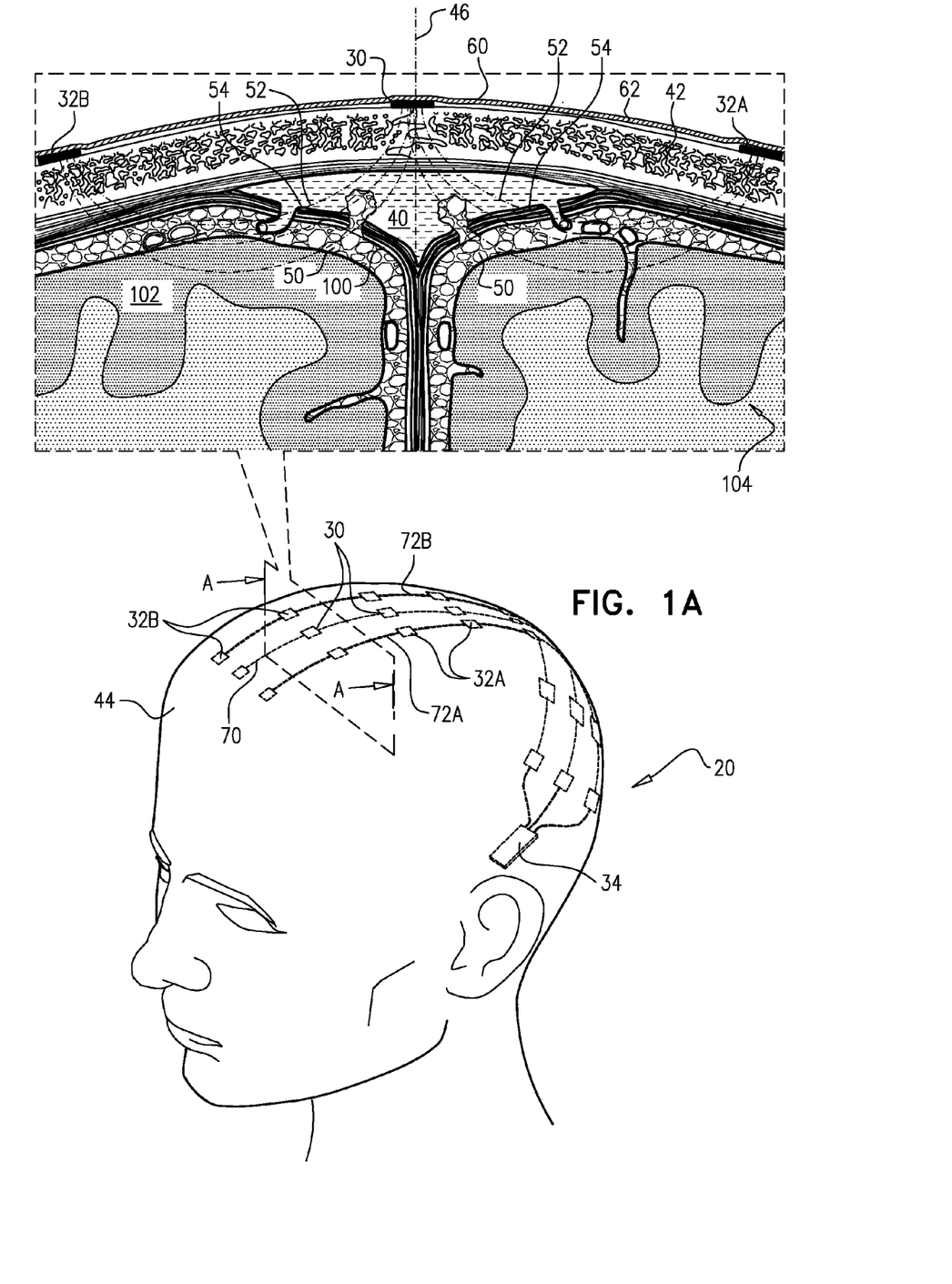
FIGS. 1A-B are schematic illustration of a system for treating Alzheimer's disease, in accordance with respective applications of the present invention.
Figure 1B:
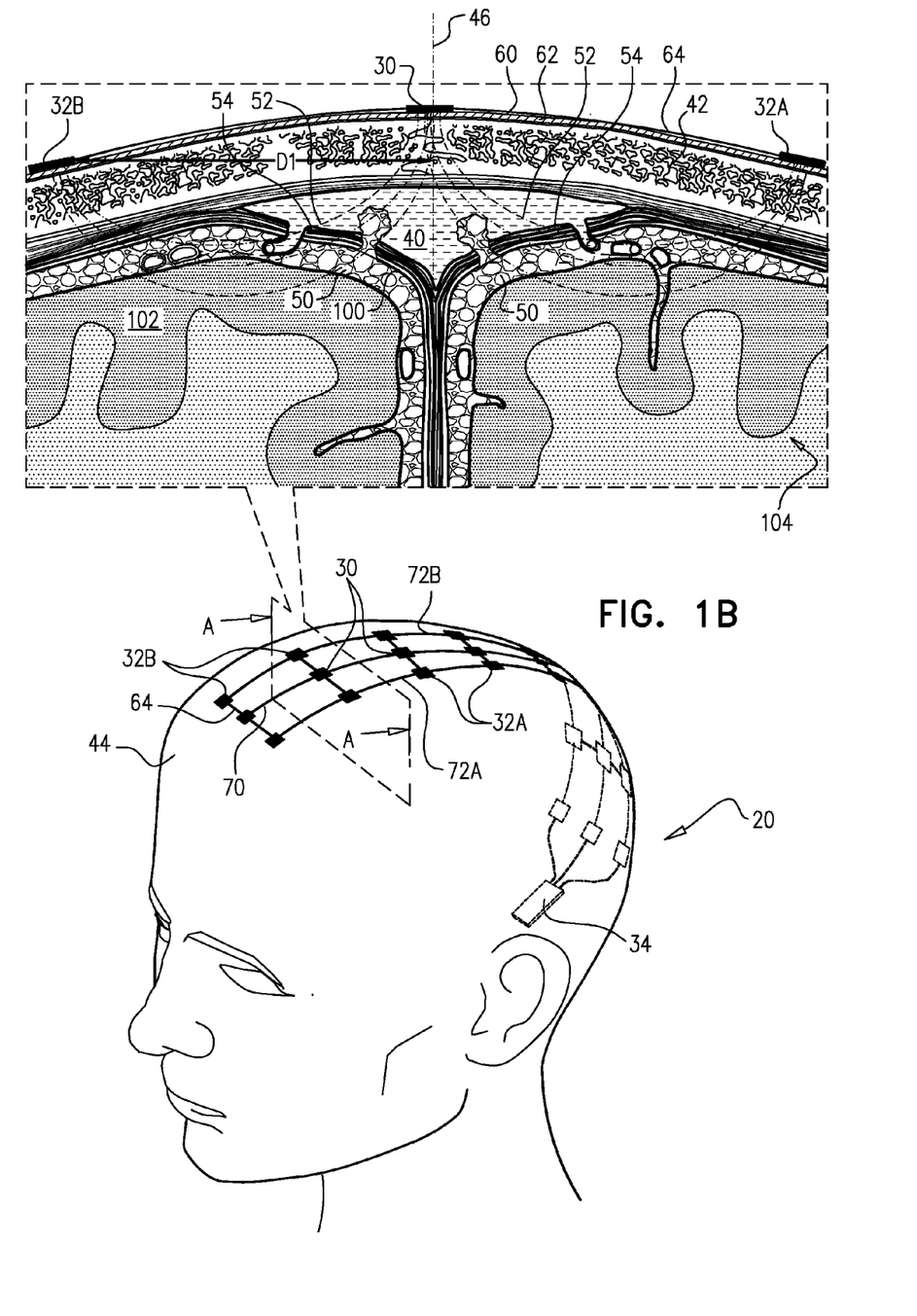

FIGS. 1A-B are schematic illustration of a system 20 for treating Alzheimer's disease, in accordance with respective applications of the present invention. System 20 comprises a plurality of midplane treatment electrodes 30, such as at least 5, no more than 20, and/or between 5 and 20 midplane treatment electrodes 30. System 20 further comprises a plurality of lateral treatment electrodes 32, such as at least 5, no more than 40, and/or between 5 and 40 lateral treatment electrodes 32, such as between 5 and 20 lateral treatment electrodes 32, or between 10 and 40 lateral treatment electrodes. For some applications, the number of each type of treatment electrode is determined based on the size of the head of the subject. For some applications, system 20 comprises twice as many lateral treatment electrodes 32 as midplane treatment electrodes 30. System 20 further comprises control circuitry 34, which is electrically coupled to the treatment electrodes.

For some applications, a method for treating Alzheimer's disease comprises:
  disposing midplane treatment electrodes 30 over a superior sagittal sinus 40, outside and in electrical contact with a skull 42 of a head 44 of a subject identified as at risk of or suffering from Alzheimer's disease;
  disposing lateral treatment electrodes 32 at a distance D1 of between 1 and 12 cm of a sagittal midplane 46 of skull 42 (labeled in FIG. 1B; distance D1 is measured in a straight line from a closest portion of each treatment electrode to sagittal midplane 46, rather than along the curvature of skull 42); and
  treating the subject by electroosmotically driving fluid from a subarachnoid space 50 to superior sagittal sinus 40, by activating control circuitry 34 to apply one or more treatment currents between (a) one or more of midplane treatment electrodes 30 and (b) one or more of lateral treatment electrodes 32 (each of the treatment currents is schematically illustrated in the figures by a plurality of current lines 52).

As used in the present application, including in the claims, "over the superior sagittal sinus" means aligned with the superior sagittal sinus at a location more superficial than the superior sagittal sinus, i.e., at a greater distance from a center of the head. As used in the present application, including in the claims, "treating" includes both treating a subject already diagnosed with Alzheimer's disease, as well as preventing the development of Alzheimer's disease in a subject not diagnosed with the disease and/or asymptomatic for the disease.

For some applications, treating the subject comprises facilitating clearance of amyloid beta from subarachnoid space 50 to superior sagittal sinus 40 by electroosmotically driving the fluid from subarachnoid space 50 to superior sagittal sinus 40. Alternatively or additionally, for some applications, treating the subject comprises facilitating clearance of metal ions from subarachnoid space 50 to superior sagittal sinus 40 by electroosmotically driving the fluid from subarachnoid space 50 to superior sagittal sinus 40. Application of the treatment currents causes a potential difference between subarachnoid space 50 and superior sagittal sinus 40, which causes movement of the amyloid beta and/or metal ions from subarachnoid space 50 to superior sagittal sinus 40.

For some applications, the one or more treatment currents applied using midplane treatment electrodes 30 and lateral treatment electrodes 32 pass between subarachnoid space 50 and superior sagittal sinus 40, via inferolateral surfaces 54 of superior sagittal sinus 40. For some of these applications, at least 40%, e.g., at least 75' or at least 90%, of the treatment currents pass between subarachnoid space 50 and superior sagittal sinus 40, via inferolateral surfaces 54 of superior sagittal sinus 40. For the applications described immediately above, the locations of midplane treatment electrodes 30 and/or lateral treatment electrodes 32 are typically selected such that the one or more treatment currents pass through inferolateral surfaces 54. For example, for configurations in which lateral treatment electrodes 32 are disposed outside and in electrical contact with skull 42, such as described with reference to FIGS. 1A-B, lateral treatment electrodes 32 may be disposed at distance D1 of at least 4 cm, no more than 12 cm, and/or between 4 and 12 cm of sagittal midplane 46 of skull 42; for configurations in which lateral treatment electrodes 32 are implanted under an arachnoid mater 100 of the subject, such as described with reference to FIG. 2, lateral treatment electrodes 32 may be disposed at least 1 cm, no more than 3 cm, and/or between 1 and 3 cm of sagittal midplane 46 of skull 42.

Typically, control circuitry 34 is activated to configure midplane treatment electrodes 30 as cathodes, and lateral treatment electrodes 32 as anodes. Alternatively, for some applications, control circuitry 34 is activated to configure midplane treatment electrodes 30 as anodes, and lateral treatment electrodes 32 as cathodes, such as for electroosmotically driving fluid from superior sagittal sinus 40 to subarachnoid space 50.

For some applications, at least five midplane treatment electrodes 30 are disposed over superior sagittal sinus 40. Alternatively or additionally, for some applications, at least five lateral treatment electrodes 32 between 1 and 12 cm of sagittal midplane 46 of skull 42. For some applications, each of lateral treatment electrodes 32 is disposed between 1 and 12 cm of at least one of midplane treatment electrodes 30.

For some applications, midplane treatment electrodes 30 are disposed within 10 mm of sagittal midplane 46 of skull 42. Alternatively or additionally, for some applications, midplane treatment electrodes 30 are disposed such that at least one of midplane treatment electrodes 30 is at least 5 mm from another one of midplane treatment electrodes 30, no more than 20 mm from another one of midplane treatment electrodes 30, and/or between 5 and 30 mm from another one of midplane treatment electrodes 30. For some applications, at least one of lateral treatment electrodes 32 is disposed is at least 5 mm from another one of lateral treatment electrodes 32.

For some applications, such as shown in FIG. 1A, midplane treatment electrodes 30 are implanted under skin 62 of head 44. For other applications, such as shown in FIG. 1B, midplane treatment electrodes 30 are disposed outside head 44, such as on an external surface 60 of head 44. For some applications, system 20 further comprises a midplane lead 70, along which midplane treatment electrodes 30 are disposed (e.g., fixed). Midplane lead 70 is disposed outside skull 42 in order to dispose midplane treatment electrodes 30 over superior sagittal sinus 40. For some applications in which midplane treatment electrodes 30 are implanted under skin 62, the implantation is performed by introducing midplane lead 70 through an incision in skin 62, typically at a posterior site of the head, and tunneling the midplane lead toward an anterior site of the head, such as near the forehead. Optionally, each of midplane treatment electrodes 30 is inserted through a respective incision in skin 62, and connected to midplane lead 70.

For some applications, the method further comprises implanting control circuitry 34 under skin of the subject, such as under skin 62 of head 44, or elsewhere in the subject's body.

For some applications, such as shown in FIGS. 1A-B, lateral treatment electrodes 32 are disposed outside and in electrical contact with skull 42. For some of these applications, lateral treatment electrodes 32 are implanted under skin 62 of head 44, such as shown in FIG. 1A. Alternatively, lateral treatment electrodes 32 are disposed outside head 44, such as on external surface 60 of head 44, such as shown in FIG. 1B. For some of these applications, lateral treatment electrodes 32 may be disposed at least 4 cm, no more than 12 cm, and/or between 4 and 12 cm of sagittal midplane 46 of skull 42. (As used in the present application, including in the claims, all specified ranges include their endpoints.) Such positioning may generate one or more treatment currents that pass between subarachnoid space 50 and superior sagittal sinus 40, via inferolateral surfaces 54 of superior sagittal sinus 40, as described above. For some applications, system 20 further comprises a lateral lead 72, along which lateral treatment electrodes 32 are disposed (e.g., fixed). Lateral lead 72 is disposed outside skull 42, typically within 1 and 12 cm of sagittal midplane 46 of skull 42, in order to dispose lateral treatment electrodes 32. For some applications in which lateral treatment electrodes 32 are implanted under skin 62, the implantation is performed by introducing lateral lead 72 through an incision in skin 62, typically at a posterior site of the head, and tunneling the lateral lead toward an anterior site of the head, such as near the forehead. Optionally, each of lateral treatment electrodes 32 is inserted through a respective incision in skin 62, and connected to lateral lead 72. For some applications, instead of providing lateral lead 72, lateral treatment electrodes 32 are instead coupled to midplane lead 70. Midplane lead 70 is introduced with the lateral electrodes constrained, and, the lateral electrodes are configured upon release to extend laterally, typically automatically. This configuration may also be used for applications in which both left and right lateral electrodes are provided, as described hereinbelow.

For some applications, control circuitry 34 is activated to independently apply the treatment currents between respective pairs of midplane treatment electrodes 30 and lateral treatment electrodes 32. Such independent application of the currents allows continued effective operation of system 20 even if a low resistance should develop between the electrodes of one of the pairs (e.g., because of anatomical variations). For some of these applications, in order to enable such independent application of the currents, midplane lead 70 comprises a plurality of conductive wires corresponding to a number of midplane treatment electrodes 30, and lateral lead 72 comprises a plurality of conductive wires corresponding to a number of lateral treatment electrodes 32. Alternatively, control circuitry 34 and the electrodes implement electrical multiplexing, as is known in the art, in which case each of the leads need only comprise a single conductive wire. Alternatively, for some applications, all of midplane treatment electrodes 30 are electrically coupled to one another (such as by a single conductive wire in the midplane lead), and all of lateral treatment electrodes 32 are electrically coupled to one other (such as by a single conductive wire in the lateral lead).

For some applications of the configuration shown in FIG. 1B, system 20 further comprises one or more thin elongate support elements 64, which couple lateral leads 72 to midplane lead 70, in order to provide proper spacing and alignment between the midplane electrodes and the lateral electrodes. Support elements 64 are typically non-conductive.

For some applications, control circuitry 34 is configured to apply the one or more treatment currents with an average amplitude of between 1 and 3 milliamps. (The resulting voltage is typically greater in the configuration shown in FIGS. 1A-B than in the configuration shown in FIG. 2, because the one or more treatment currents pass through skull 42 twice.)

For some applications, control circuitry 34 is activated to apply the one or more treatment currents as direct current, typically as a plurality of pulses, for example at greater than 500 Hz and/or less than 2 kHz, e.g., at 1 kHz. For some applications, a duty cycle of the pulses is above 90%, and for some applications pulses are not used but instead an effective duty cycle of 100% is utilized. Typically, but not necessarily, the duty cycle is 90% or lower, because a given level of applied voltage produces higher current in the tissue if the capacitance in the tissue is allowed to discharge between pulses.

For some applications, control circuitry 34 is activated to apply the one or more treatment currents in sessions, each of which has a duration of several seconds or several minutes, or continuously for longer periods (e.g., 30 minutes). For some applications, the one or more treatment currents are not applied for a period that is at least an hour. Optionally, control circuitry 34 is activated to apply the one or more treatment currents only when the subject is sleeping, such as to inhibit any sensations that may be associated with application of the one or more treatment currents. For some applications, power for activating and/or charging control circuitry 34 is transmitted from a wireless energy transmitter in a hat, such as described hereinbelow with reference to FIG. 3, or from a wireless energy transmitter in, under, or above a mattress. For some applications, control circuitry 34 is activated to apply the one or more treatment currents according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the treatment voltage is not applied are provided in the pre-selected schedule.

For some applications, lateral treatment electrodes 32 comprise left lateral treatment electrodes 32A and right lateral treatment electrodes 32B. Left lateral treatment electrodes 32A are disposed left of sagittal midplane 46 of skull 42, and right lateral treatment electrodes 32B are disposed right of sagittal midplane 46 of skull 42. For some applications, control circuitry 34 is activated to configure midplane treatment electrodes 30 as cathodes, and left and right lateral treatment electrodes 32A and 32B as left and right anodes, respectively.

For some applications, left lateral treatment electrodes 32A are disposed such that at least one of left lateral treatment electrodes 32A is at least 1 cm, no more than 5 cm, and/or between 1 and 5 cm (e.g., 3 cm) from another one of left lateral treatment electrodes 32A, and/or right lateral treatment electrodes 32B are disposed such that at least one of right lateral treatment electrodes 32B is at least 1 cm, no more than 5 cm, and/or between 1 and 5 cm (e.g., 3 cm) from another one of right lateral treatment electrodes 32B. Alternatively or additionally, for some applications, left lateral treatment electrodes 32A are disposed such that longitudinally-adjacent ones of the electrodes are disposed at least 1 cm, no more than 5 cm, and/or between 1 and 5 cm (e.g., 3 cm) from each other, and/or right lateral treatment electrodes 32B are disposed such that longitudinally-adjacent ones of the electrodes are disposed at least 1 cm, no more than 5 cm, and/or between 1 and 5 cm (e.g., 3 cm) from each other. For some applications, at least five left lateral treatment electrodes 32A are disposed left of sagittal midplane 46 of skull 42, and/or at least five right lateral treatment electrodes 32B are disposed right of sagittal midplane 46 of skull 42.

As mentioned above, for some applications, system 20 further comprises midplane lead 70, along which midplane treatment electrodes 30 are disposed (e.g., fixed). Midplane lead 70 is disposed outside skull 42 in order to dispose midplane treatment electrodes 30. For some of these applications, system 20 further comprises (a) a left lateral lead 72A, along which left lateral treatment electrodes 32A are disposed (e.g., fixed), and (b) a right lateral lead 72B, along which right lateral treatment electrodes 32B are disposed (e.g., fixed). Left lateral lead 72A is disposed outside skull 42, typically within 1 and 12 cm of sagittal midplane 46 of skull 42, in order to dispose left lateral treatment electrodes 32A. Right lateral lead 72B is disposed outside skull 42, typically within 1 and 12 cm of sagittal midplane 46 of skull 42, in order to dispose right lateral treatment electrodes 32B.

For some applications, control circuitry 34 is activated to independently apply the treatment currents between respective pairs of midplane and left lateral treatment electrodes 30 and 32A, and between respective pairs of midplane and right lateral treatment electrodes 30 and 32B. For example, control circuitry 34 may be activated to apply the treatment currents between each of the midplane treatment electrodes 30 and both (a) a corresponding one of left lateral treatment electrodes 32A and (b) a corresponding one of right lateral treatment electrodes 32B. For some of these applications, in order to enable such independent application of the treatment currents, midplane lead 70 comprises a plurality of conductive wires corresponding to a number of midplane treatment electrodes 30, left lateral lead 72A comprises a plurality of conductive wires corresponding to a number of left lateral treatment electrodes 32A, and right lateral lead 72B comprises a plurality of conductive wires corresponding to a number of right lateral treatment electrodes 32B. Alternatively, control circuitry 34 and the electrodes implement electrical multiplexing, as is known in the art, in which case each of the leads need only comprise a single conductive wire. Alternatively, for some applications, all of midplane treatment electrodes 30 are electrically coupled to one other (such as by a single conductive wire in the midplane lead), all of left lateral treatment electrodes 32A are electrically coupled to one other (such as by a single conductive wire in the left lateral lead), and all of right lateral treatment electrodes 32B are electrically coupled to one other (such as by a single conductive wire in the right lateral lead).

For example, control circuitry 34 may be activated to apply:
- a first treatment current between a first one of midplane treatment electrodes 30 and a first one of left lateral treatment electrodes 32A,
- a second treatment current between the first one of midplane treatment electrodes 30 and a first one of right lateral treatment electrodes 32B,
- a third treatment current between a second one of midplane treatment electrodes 30 and a second one of left lateral treatment electrodes 32A, and
- a fourth treatment current between the second one of midplane treatment electrodes 30 and a second one of right lateral treatment electrodes 32B.

Typically, control circuitry 34 is activated to configure midplane treatment electrodes 30 as cathodes, and left and right lateral treatment electrodes 32A and 32B as left and right anodes, respectively.

Figure 2:
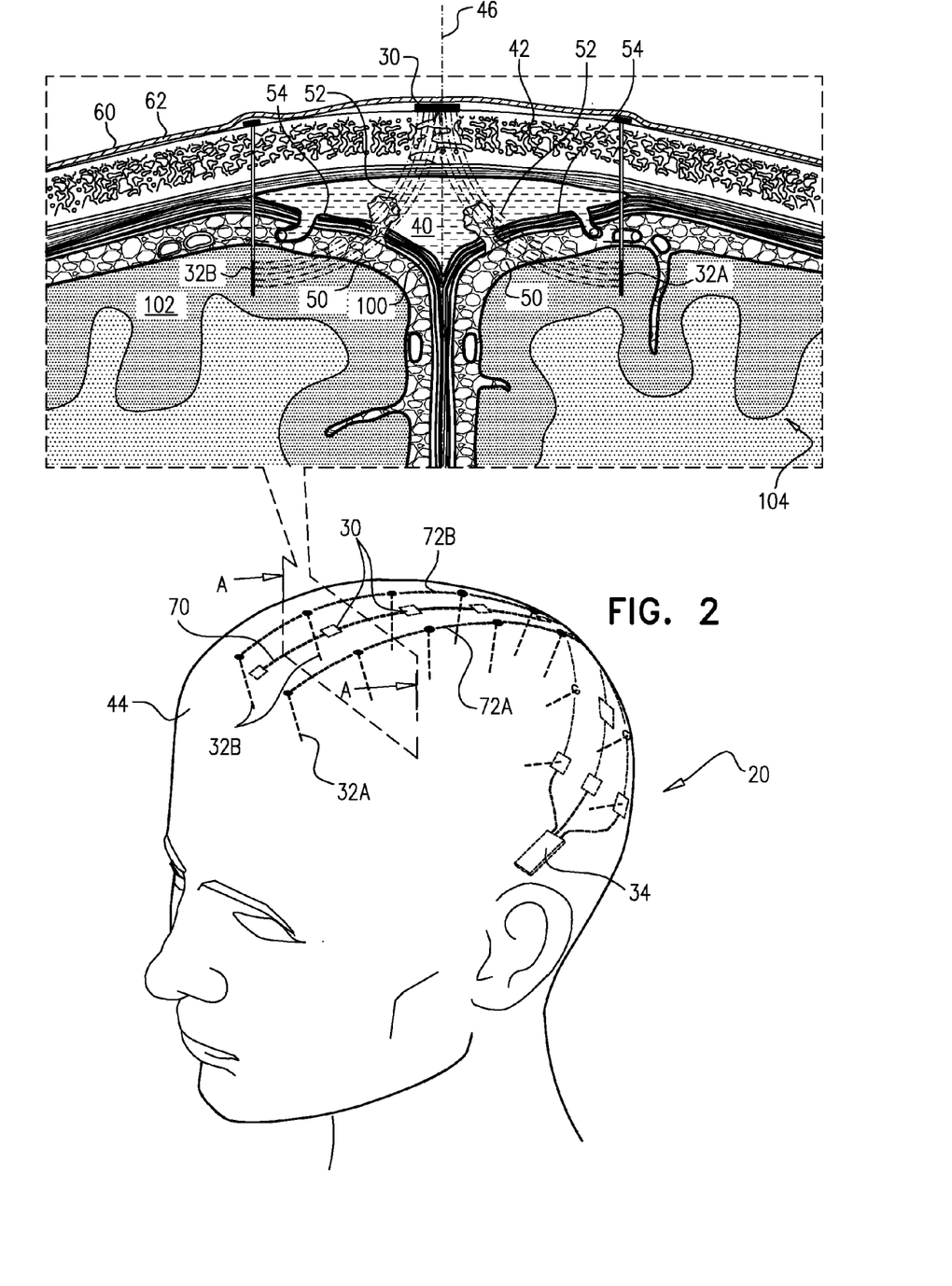
FIG. 2 is a schematic illustration of another configuration of the system of FIGS. 1A-B, in accordance with an application of the present invention.

Reference is now made to FIG. 2, which is a schematic illustration of another configuration of system 20, in accordance with an application of the present invention. In this configuration, lateral treatment electrodes 32 are implanted under arachnoid mater 100 of the subject, such as in subarachnoid space 50, in gray matter 102, or in white matter of a brain 104 of the subject. For example, lateral treatment electrodes 32 may comprise needle electrodes, as is known in the art. This configuration may implement any of the techniques described hereinabove with reference to FIGS. 1A-B, mutatis mutandis.

For some of these applications, lateral treatment electrodes 32 are disposed at least 1 cm, no more than 3 cm, and/or between 1 and 3 cm of sagittal midplane 46 of skull 42. Such positioning may generate the treatment currents that pass between subarachnoid space 50 and superior sagittal sinus 40, via inferolateral surfaces 54 of superior sagittal sinus 40, as described above. For some applications, each of lateral treatment electrodes 32 is disposed between 1 and 3 cm of at least one of midplane treatment electrodes 30. For some applications, each of lateral treatment electrodes 32 is disposed between 1 and 3 cm of one of midplane treatment electrodes 30 that is closest to the lateral treatment electrode.

For some applications, a surgical technique for implanting lateral treatment electrodes 32 comprises:
- drilling a hole through skull 42, typically at a posterior site of the skull, and typically between 1 and 3 cm of sagittal midplane 46 of skull 42;
- introducing a catheter through the hole and into subarachnoid space 50 or the gray or white matter of the brain, while a lateral lead 72 is disposed along the catheter;
- advancing the catheter within the brain to a more anterior site, such as near the forehead; and
- withdrawing the catheter while leaving lateral lead 72 in place within the brain.

Lateral lead 72 is then electrically coupled to control circuitry 34, if not previously coupled prior to the implantation procedure.

This procedure is typically performed twice, once for each of left and right lateral leads 72A and 72B. Therefore, only two holes need to be made through the skull in order to implant all of lateral treatment electrodes 32. A similar procedure may be employed for implanting midplane lead 70 under skin 62; alternatively, midplane lead 70 is implanted without the use of a catheter, such as by tunneling, as described hereinabove with reference to FIG. 1A.

Figure 3:
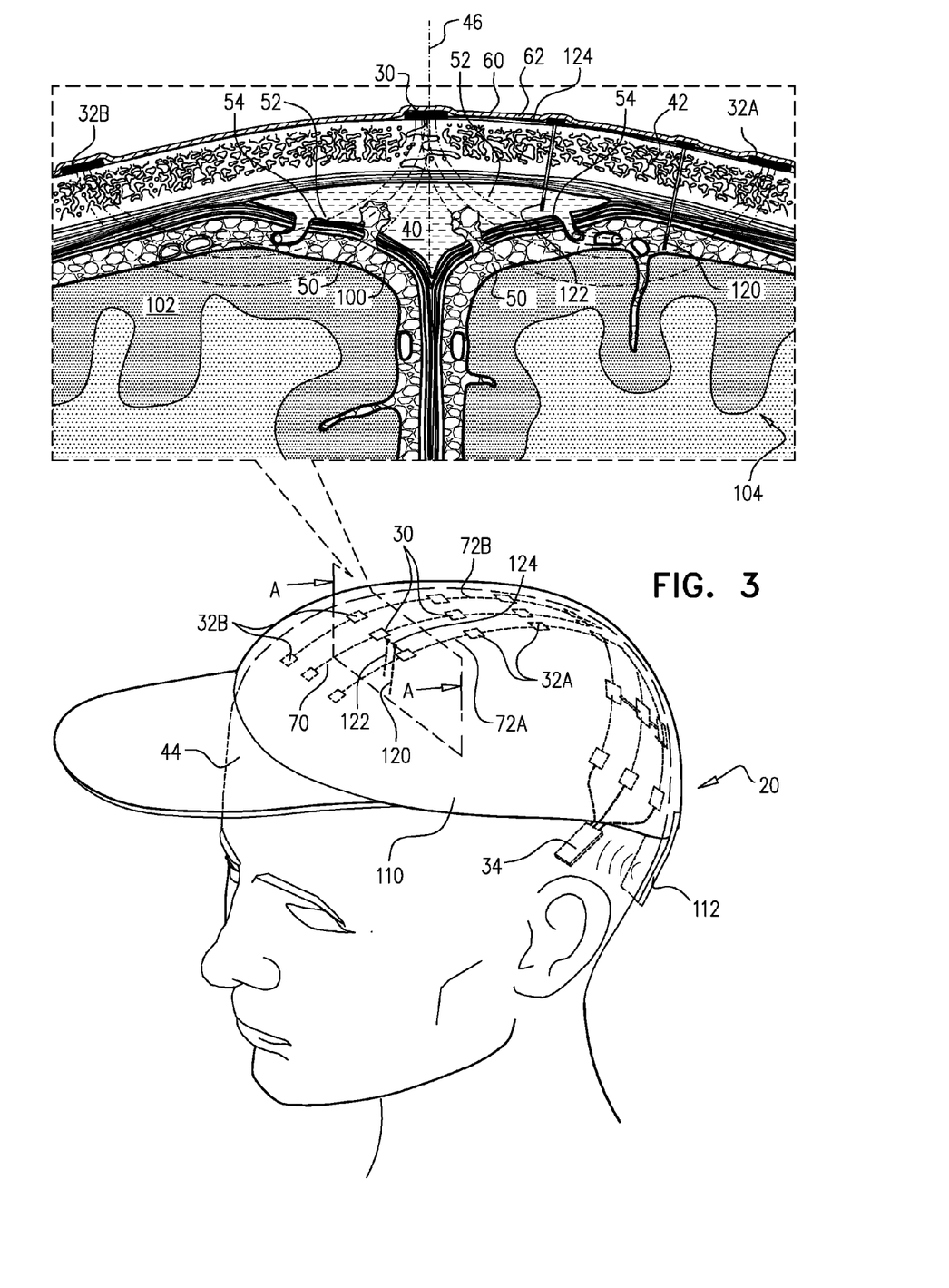
FIG. 3 is a schematic illustration of yet another configuration of the system of FIG. 1A, in accordance with an application of the present invention.

Reference is now made to FIG. 3, which is a schematic illustration of yet another configuration of system 20, in accordance with an application of the present invention. Although this configuration is illustrated for the configuration of system 20 shown in FIG. 1A, it may also be used with the configurations shown in FIGS. 1B and 2. In this configuration, electroosmotically driving the fluid comprises (a) detecting, by control circuitry 34, a voltage difference between subarachnoid space 50 and superior sagittal sinus 40, and (b) setting, by control circuitry 34, a level of the one or more treatment currents responsively to the detected voltage difference. For some applications, system 20 further comprises a single first detection electrode 120 and a single second detection electrode 122. Single first detection electrode 120 is implanted in subarachnoid space 50, and single second detection electrode 122 is implanted in superior sagittal sinus 40. For some applications, detecting the voltage comprises detecting, by control circuitry 34, the voltage difference between first and second detection electrodes 120 and 122.

Reference is still made to FIG. 3. For some applications, system 20 further comprises a hat 110, which comprises a wireless energy transmitter 112. When the subject wears the hat, transmitter 112 is disposed in a vicinity of control circuitry 34 (which may be implanted subcutaneously, as described above). Control circuitry 34 comprises a wireless energy receiver to receive energy transmitted by transmitter 112. Although described with reference to FIG. 3, hat 110 may also be implemented in combination with any of the other configurations of system 20 described herein, including those shown in FIGS. 1A, 1B, and 2.

Figure 4:
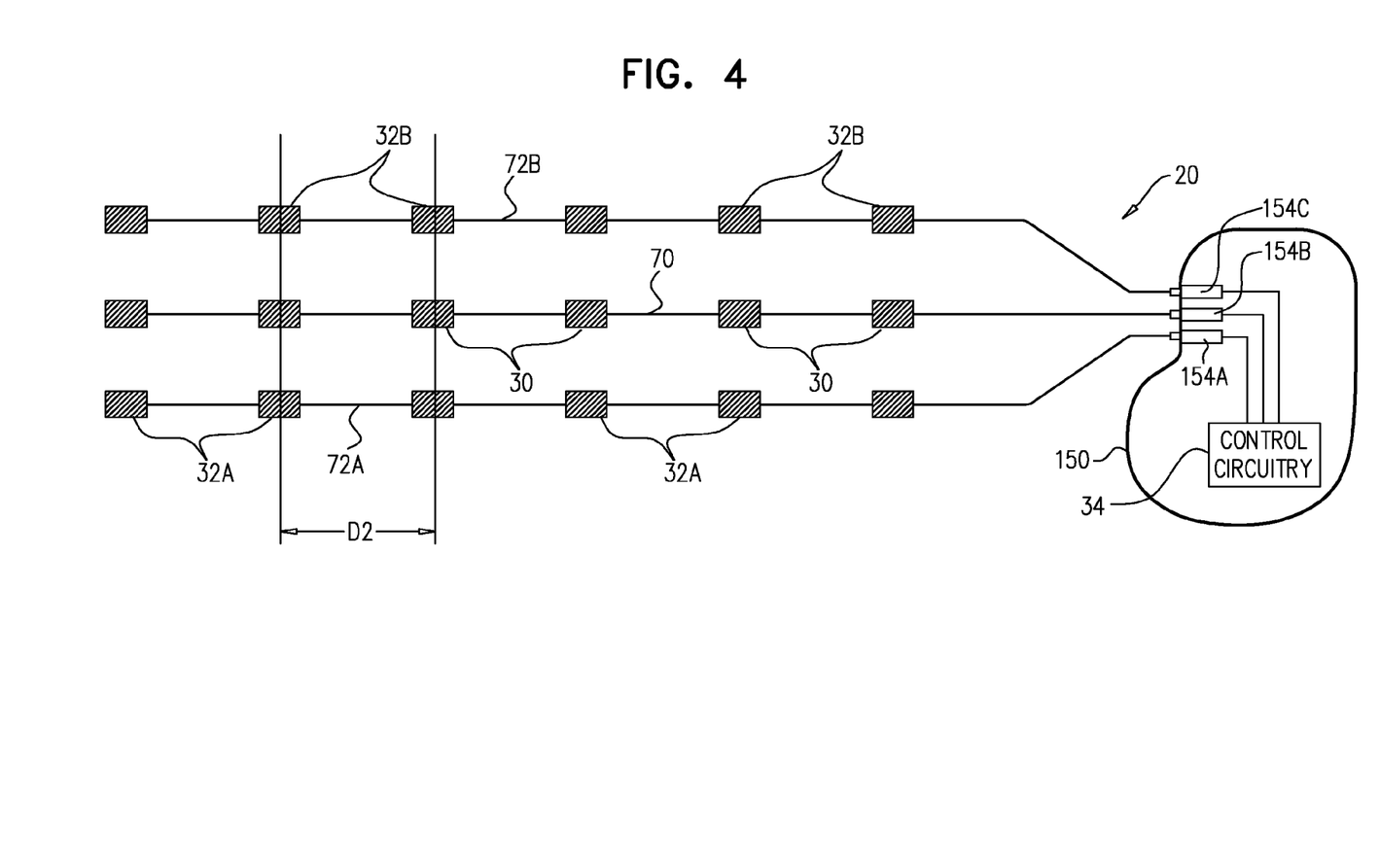
FIG. 4 is a schematic illustration of a system for treating Alzheimer's disease, in accordance with an application of the present invention.

Reference is now made to FIG. 4, which is a schematic illustration of system 20, in accordance with an application of the present invention. For some applications, system 20 comprises a housing 150, which contains control circuitry 34. For some applications, housing 150 is implantable, such as subcutaneous; for example, the housing may be similar to conventional pacemaker housings ("cans"). For some applications, housing 150 comprises first, second, and third lead interfaces 154A, 154B, and 154C, for electrical and mechanical coupling with midplane lead 70 and lateral leads 72. For example, first, second, and third lead interfaces 154A, 154B, and 154C may comprise first, second, and third ports, into which corresponding connectors of the leads are inserted. Alternatively, the leads may have hardwired connections with the lead interfaces. First, second, and third lead interfaces 154A, 154B, and 154C are also electrically coupled with control circuitry 34.

Typically, the lead interfaces are physically arranged such that second lead interface 154B is between first and third lead interfaces 154A and 154C on housing 150. Control circuitry 34 is configured to apply current through second lead interface 154B to midplane lead 70 such that midplane treatment electrodes 30 are cathodes, and to apply current through first and third lead interfaces 154A and 154B such that lateral treatment electrodes 32 are anodes.

Alternatively, for some applications, housing 150 comprises only two lead interfaces, and left and right lateral leads 72A and 72B are electrically coupled to each other so as define a single, joint connector, which is coupleable to one of the lead interfaces of the housing.

As mentioned above with reference to FIGS. 1A-B, for some applications system 20 comprises between 5 and 20 midplane treatment electrodes 30, a corresponding number of left lateral treatment electrodes 32A, and a corresponding number of right lateral treatment electrodes 32B. For some applications, an average distance D2 between (a) longitudinally-adjacent pairs of midplane treatment electrodes 30, (b) longitudinally-adjacent pairs of first lateral treatment electrodes 32A, and (c) longitudinally-adjacent pairs of second lateral treatment electrodes 32B is at least 1 cm, no more than 5 cm, and/or between 1 and 5 cm (e.g., 3 cm), measured between longitudinal midpoints of the electrodes. For some applications, each of midplane lead 70, left lateral lead 72A, and right lateral lead 72B, when fully extended, has a length of at least 10 cm, no more than 40 cm (e.g., no more than 30 cm), and/or between 10 and 40 cm (e.g., between 10 and 30 cm).

For some applications, system 20 comprises:
- exactly three leads, consisting of a midplane lead 70, a left lateral lead 72A, and a right lateral lead 72B;
- at least five midplane treatment electrodes 30, which are disposed (e.g., fixed) along midplane lead 70 at an average distance of at least 1 cm, no more than 5 cm, and/or between 1 and 5 cm (e.g., 3 cm) between longitudinally-adjacent pairs of midplane treatment electrodes 30, measured between longitudinal midpoints of midplane treatment electrodes 30;
- at least five left lateral treatment electrodes 32A, which are disposed (e.g., fixed) along left lateral lead 72A at an average distance of at least 1 cm, no more than 5 cm, and/or between 1 and 5 cm (e.g., 3 cm) between longitudinally-adjacent pairs of left lateral treatment electrodes 32A, measured between longitudinal midpoints of left lateral treatment electrodes 32A;
- at least five right lateral treatment electrodes 32B, which are disposed (e.g., fixed) along right lateral lead 72B at an average distance of at least 1 cm, no more than 5 cm, and/or between 1 and 5 cm (e.g., 3 cm) between longitudinally-adjacent pairs of right lateral treatment electrodes 32B, measured between longitudinal midpoints of right lateral treatment electrodes 32B; and
- housing 150, which comprises control circuitry 34, to which midplane treatment electrodes 30, left lateral treatment electrodes 32A, and right lateral treatment electrodes 32B are electrically coupled via midplane lead 70, left lateral lead 72A, and right lateral lead 72B, respectively.

Control circuitry 34 is configured to:
- configure midplane treatment electrodes 30 as cathodes, and left and right lateral treatment electrodes 32A and 32B as left and right anodes, respectively,
- apply respective treatment currents between (a) (i) one or more of midplane treatment electrodes 30 and (ii) one or more of left lateral treatment electrodes 32A, and (b) (i) one or more of midplane treatment electrodes 30 and (ii) one or more of right lateral treatment electrodes 32B, and
- configure the treatment currents to treat the subject by electroosmotically driving fluid from subarachnoid space 50 to superior sagittal sinus 40.

Reference is made to FIGS. 1A-4. For any of the applications described herein, system 20 may comprise:
- a single midplane treatment electrode 30, rather than a plurality of midplane treatment electrodes 30,
- a single lateral treatment electrode 32, rather than a plurality of lateral treatment electrodes 32, a single left lateral treatment electrode 32A, rather than a plurality of left lateral treatment electrodes 32A, and/or a single right lateral treatment electrode 32B, rather than a plurality of right lateral treatment electrodes 32B.

For some of these applications, any of these single electrodes comprises an elongate electrode having a length of at least 10 cm, no more than 40 cm (e.g., no more than 30 cm), and/or between 10 and 40 cm (e.g., between 10 and 30 cm); for example, the elongate electrode may comprise an electrically-non-insulated wire.

Although the techniques described hereinabove have been described as treating the subject by electroosmotically driving fluid from subarachnoid space 50 to superior sagittal sinus 40, the techniques may alternatively or additionally be used without electroosmosis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    midplane treatment electrodes, configured to be disposed over a superior sagittal sinus, outside and in electrical contact with a skull of a head of a subject identified as at risk of or suffering from Alzheimer's disease;
    lateral treatment electrodes, configured to be disposed between 1 and 12 cm of a sagittal midplane of the skull; and
    control circuitry, which is configured to treat the subject by electroosmotically driving fluid from a subarachnoid space to the superior sagittal sinus, by applying one or more treatment currents between (a) one or more of the midplane treatment electrodes and (b) one or more of the lateral treatment electrodes.

2. The apparatus according to claim 1, wherein the control circuitry is configured to treat the subject by facilitating clearance of amyloid beta from the subarachnoid space to the superior sagittal sinus by electroosmotically driving the fluid from the subarachnoid space to the superior sagittal sinus.

3. The apparatus according to claim 1, wherein the control circuitry is configured to treat the subject by facilitating clearance of metal ions from the subarachnoid space to the superior sagittal sinus by electroosmotically driving the fluid from the subarachnoid space to the superior sagittal sinus.

4. The apparatus according to claim 1, wherein the midplane treatment electrodes comprises at least five midplane treatment electrodes, which are configured to be disposed over the superior sagittal sinus.

5. The apparatus according to claim 1, wherein the control circuitry is configured to configure the midplane treatment electrodes as cathodes, and the lateral treatment electrodes as anodes.

6. The apparatus according to claim 1,
    wherein the lateral treatment electrodes comprise left lateral treatment electrodes and right lateral treatment electrodes, and
    wherein the left lateral treatment electrodes are configured to be disposed left of the sagittal midplane of the skull, and the right lateral treatment electrodes are configured to be disposed right of the sagittal midplane of the skull.

7. The apparatus according to claim 6, wherein the control circuitry is configured to configure the midplane treatment electrodes as cathodes, and the left and the right lateral treatment electrodes as left and right anodes, respectively.

8. The apparatus according to claim 6, wherein the control circuitry is configured to apply the one or more treatment currents between (a) one or more of the midplane treatment electrodes and (b) one or more of the lateral treatment electrodes by applying:
    a first treatment current between a first one of the midplane treatment electrodes and a first one of the left lateral treatment electrodes,
    a second treatment current between the first one of the midplane treatment electrodes and a first one of the right lateral treatment electrodes,
    a third treatment current between a second one of the midplane treatment electrodes and a second one of the left lateral treatment electrodes, and
    a fourth treatment current between the second one of the midplane treatment electrodes and a second one of the right lateral treatment electrodes.

9. The apparatus according to claim 1, wherein the control circuitry is configured to:
    detecting a voltage difference between the subarachnoid space and the superior sagittal sinus, and
    setting a level of the one or more treatment currents responsively to the detected voltage difference.

10. The apparatus according to claim 1, wherein the control circuitry is configured to apply the one or more treatment currents as direct currents.

11. The apparatus according to claim 10, wherein the control circuitry is configured to apply the one or more direct currents as a plurality of pulses.

12. The apparatus according to claim 1, wherein the lateral treatment electrodes are configured to be disposed outside and in electrical contact with the skull.

13. The apparatus according to claim 12, wherein the lateral treatment electrodes are configured to be disposed outside the head.

14. The apparatus according to claim 12, wherein the lateral treatment electrodes are configured to be implanted under skin of the head.

15. The apparatus according to claim 1, wherein the midplane treatment electrodes are configured to be disposed outside the head.

16. The apparatus according to claim 1, wherein the midplane treatment electrodes are configured to be implanted under skin of the head.

17. The apparatus according to claim 1, wherein the lateral treatment electrodes are configured to be implanted under an arachnoid mater of the subject.

18. The apparatus according to claim 17, wherein the lateral treatment electrodes are configured to be disposed in the subarachnoid space.

19. The apparatus according to claim 17, wherein the lateral treatment electrodes are configured to be disposed in gray or white matter of a brain of the subject.

20. The apparatus according to claim 1, wherein the control circuitry is configured to apply the one or more treatment currents with an average amplitude of between 1 and 3 milliamps.

21. The apparatus according to claim 1, wherein the control circuitry is configured to be implanted under skin of the subject.

22. The apparatus according to claim 1, wherein the control circuitry is configured to:

detect a voltage difference between the subarachnoid space and the superior sagittal sinus, and set a level of the one or more treatment currents responsively to the detected voltage difference.

23. Apparatus comprising:

one or more midplane treatment electrodes, configured to be disposed over a superior sagittal sinus, outside and in electrical contact with a skull of a head of a subject identified as at risk of or suffering from Alzheimer's disease;

one or more lateral treatment electrodes, configured to be disposed between 1 and 12 cm of a sagittal midplane of the skull; and control circuitry, which is configured to treat the subject by electroosmotically driving fluid from a subarachnoid space to the superior sagittal sinus, by applying one or more treatment currents between (a) one or more of the midplane treatment electrodes and (b) one or more of the lateral treatment electrodes.

24. The apparatus according to claim 23, wherein the one or more lateral treatment electrodes comprise one or more left lateral treatment electrodes and one or more right lateral treatment electrodes, wherein the one or more left lateral treatment electrodes are configured to be disposed left of the sagittal midplane of the skull, and the one or more right lateral treatment electrodes are configured to be disposed right of the sagittal midplane of the skull, and wherein the control circuitry is configured to configure the one or more midplane treatment electrodes as one or more cathodes, the one or more left lateral treatment electrodes as one or more left anodes, and the one or more right lateral treatment electrodes as one or more right anodes.

* * * * *